United States Patent [19]
Gilbert

[11] 3,987,806
[45] Oct. 26, 1976

[54] DENTAL FLOSS APPLICATOR
[76] Inventor: Phylis L. Gilbert, 825 S. College, Nevada, Mo. 64772
[22] Filed: Mar. 24, 1975
[21] Appl. No.: 561,156

[52] U.S. Cl. ................................................ 132/91
[51] Int. Cl.² ..................................... A61C 15/00
[58] Field of Search ............ 132/89, 91, 92 A, 92 R

[56] References Cited
UNITED STATES PATENTS

| | | | |
|---|---|---|---|
| 1,661,472 | 3/1928 | Gilbert | 132/92 R |
| 2,013,143 | 9/1935 | Getz | 132/92 R |
| 3,759,273 | 9/1973 | Knaus | 132/92 R |
| 3,828,804 | 8/1974 | Ely | 132/91 |
| D187,132 | 2/1960 | Griffin | D24/1 |

Primary Examiner—G.E. McNeill
Attorney, Agent, or Firm—Fishburn, Gold & Litman

[57] ABSTRACT

A dental floss applicator having an elongate base member with one end portion forming a handle and diverging fingers or extenders at the other end forming a U-shaped structure with a finger spacing permitting the receiving of a person's molar tooth therebetween. The fingers have open slots or recesses in the ends and there are shoulders on opposed sides of the base member and a floss anchor on the base member spaced from the fingers providing for a dental floss strand to extend across the space between the finger ends and along said fingers to the shoulders and then in crossing relation to opposite sides of the base member to the floss anchor.

1 Claim, 6 Drawing Figures

DENTAL FLOSS APPLICATOR

This invention relates to tooth cleaning devices and more particularly to a dental floss applicator which holds a strand of fine diameter filamentary material called dental floss for insertion between teeth for removing particles which are difficult to remove by normal brushing.

It has been well known that dental floss could be used to aid in cleaning between teeth by running the floss between the teeth. It has been common to tension a length of floss between the user's fingers which must then be inserted to some extent into the mouth in order to apply the floss and move same between teeth, however, such methods are relatively awkward operations, although reasonably effective in removing food particles that would be impossible to remove with an ordinary toothbrush. There have been many attempts to develop a floss holder that would permit the user to apply the floss wherein the holder would be held by one hand and it would not be necessary to insert the person's finger into his mouth. However, the known holders are complex structures, cumbersome to use and have inadequate control over the portion of the strand of floss being used on the teeth. Furthermore, removal of particles is helpful, but that alone is not sufficient for proper dental hygiene as there is commonly a coating or material on teeth called "plaque" that is detrimental. Peridontal diseases are normally caused by plaque building up on the surface of the teeth at the gums and this build-up on the surface of the teeth tends to spread toward to root of the teeth damaging the connection between the gums and the teeth. Dental floss can be used to remove some of the plaque, however, dental floss holders heretofore available have not been well-suited for cleaning and removal of plaque in all of the areas particularly on tooth surfaces at the gum area.

The principal objects of the present invention are: to provide a dental floss applicator that includes a conveniently hand-held member with a pair of fingers or extenders having a spacing to receive a person's molar tooth therebetween and having a strand of dental floss stretched in a straight line between the fingers and arranged for movement between teeth to engage with the surface thereof for removing particles, plaque and the like; to provide a dental floss applicator which may be manufactured in one piece; to provide such an applicator having a finger and floss arrangement relative to the handle portion whereby it may be used without obstructing the view of the floss engaging the teeth thereby facilitating control of the movement of the floss; to provide such an applicator wherein the fingers diverge outwardly from an end portion of an elongate handle and said fingers are bar like portions having substantially greater width than thickness providing rigidity in a direction parallel with the elongate handle member with any flexibility being unidirectional of one finger toward the other; to provide such an applicator with floss receiving recesses or slots in the free ends of the fingers and shoulder portions on the elongate member adjacent the fingers that cooperate with a floss anchoring member spaced therefrom to hold a strand of floss positioned to extend between the fingers with a desired tension; to provide such an applicator with a handle portion having a cavity with a removable cover for holding a spool providing a supply of dental floss; and to provide a dental floss applicator that is efficiently and conveniently used and that is economical to manufacture, capable of long operating life, and particularly well adapted for its proposed use.

Other objects and advantages of this invention will become apparent from the following description taken in connection with the accompanying drawings wherein are set forth by way of illustration and example certain embodiments of this invention.

The drawings constitute a part of this specification and include exemplary embodiments of the present invention and illustrate various objects and features of the apparatus.

Figure 1:
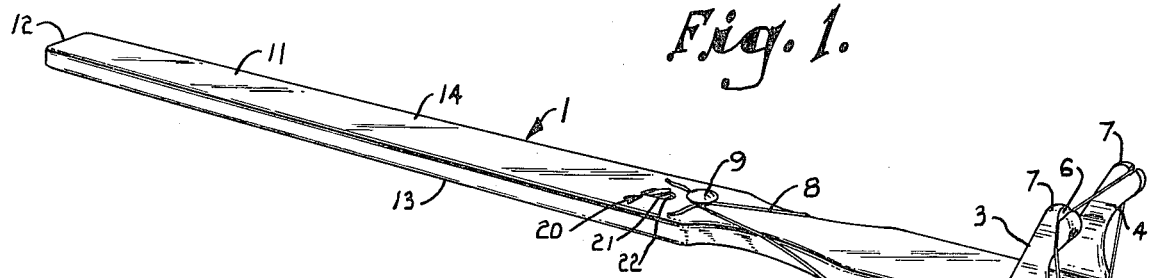
FIG. 1 is a perspective view of a dental floss applicator with a strand of floss secured in operative position.
Figure 2:
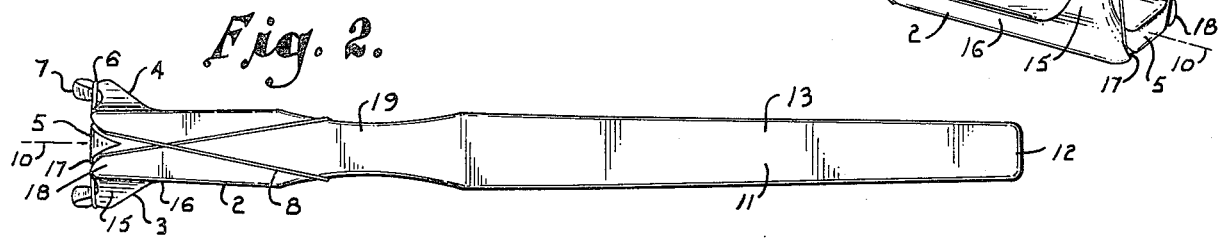
FIG. 2 is a top plan view of the applicator.
Figure 3:
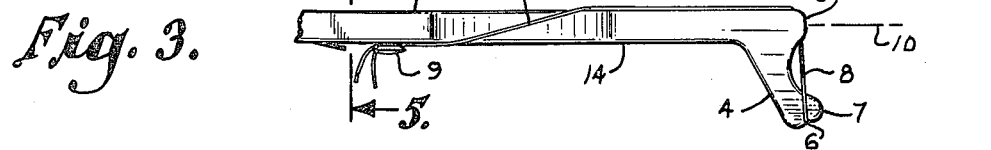
FIG. 3 is a fragmentary side elevational view of the applicator.
Figure 4:
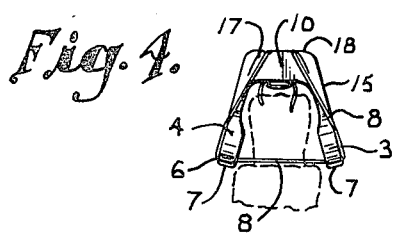
FIG. 4 is an end view of the applicator looking toward the finger end thereof.
Figure 5:
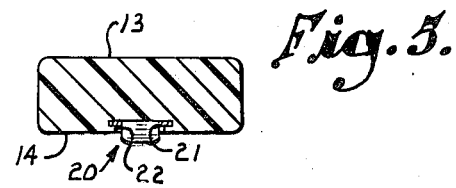
FIG. 5 is an enlarged fragmentary view through the applicator on the line 5—5, FIG. 3 showing the mounting of the floss cutter therein.

Referring more in detail to the drawings:

As required, detailed embodiments of the present invention are disclosed herewith, however, it is to be understood that the disclosed embodiments are merely exemplary of the invention which may be embodied in various forms. Therefore, specific structural and functional details disclosed herein are not to be interpreted as limited, but merely as a basis for the claims and as a representative basis for teaching one skilled in the art to variously employ the present invention in virtually any appropriately detailed structure.

The reference numeral 1 generally designates a dental floss holder having an elongate member 2 provided with spaced fingers or extenders 3 and 4 extending therefrom adjacent one end 5 thereof. The fingers 3 and 4 diverge and have a spacing therebetween to permit receiving a person's molar tooth therebetween. The fingers 3 and 4 have dental floss receiving portions 6 at free ends 7 whereby a strand of dental floss 8 extends between said receiving portions 6 spanning the space between the fingers 3 and 4. The strand of floss extends along the fingers to the elongate member and then to an anchoring member 8 for securing ends of the dental floss strand to hold same in place with a desired tension. The elongate member 2 and fingers 3 and 4 are arranged whereby the elongate member 2 may be gripped remote from the fingers and the finger portions with the strand of floss 8 thereon inserted into a mouth to move said strand of floss between adjacent teeth and to maneuver same to remove food particles and also plaque from the teeth. The fingers extend outwardly from the elongate member whereby the floss strand portion 8 between the fingers is spaced from the longitudinally axial line 10 of the elongate member in a manner to facilitate handling the applicator and provide a view of the cleaning movement of the dental floss.

The dental floss applicator as illustrated in FIGS. 1 to 5 inclusive may have the elongate member 2 and fingers 3 and 4 made in one piece preferably of a suitable synthetic resin that is easily cleaned and maintained sanitary and that has rigidity in thicker sections. In the structure illustrated, the member 2 has a handle portion 11 adjacent the other end 12 of said elongate member 2. It is preferred that the portion between the handle portion 11 and the one end 5 have opposed substantially flat surfaces 13 and 14 whereby the width thereof is greater than the thickness. The fingers 3 and 4 extend outwardly relative to the flat surface 14 with the outer surfaces 15 of the fingers preferably merging into opposed side surfaces 16 of the base member adjacent the one end 5.

The fingers 3 and 4 preferably are bar-like members having a greater width than thickness whereby the fingers are relatively rigid in the direction of the axial line 10 of the elongate member 2 and each has uni-directional flexibility toward the other finger. In the illustrated structure, the fingers 3 and 4 are also inclined away from the handle portion, the angle between the fingers and the longitudinal axial line 10 of the base member being 90° or more and preferably an obtuse angle. The free ends or tips 7 of the fingers have the floss receiving portions 6 therein and in the illustrated structure the portions 6 are recess slots or slits whereby the strand of floss 8 can be engaged therein and held against movement in the direction of the axial line 10 of the member 2.

The one end portion 5 of the elongate member 2 and/or adjacent portions of the fingers have grooves, recesses, or channels 17 to receive the strand of dental floss and define a path therefore. The grooves or recesses 17 are arranged to provide shoulders 18 engaged by the floss strand in order that the strands may extend therefrom towards the handle portion 11 of the base member. The anchor member 9 is a suitable lug or projection fixed relative to the base member 2 and in the illustrated structure the anchor 9 extends from the surface 14 adjacent the handle portion 11. The base member between the anchor member 9 and the fingers 3 and 4 is reduced in width to provide portions 19 having the floss strand extending therethrough to aid in guiding and positioning the strand extending from the shoulders 18 to the anchor member 9. It is preferred that the strand cross on the surface 13 between the shoulders 18 and recessed or narrow portions 19 of the base member.

The base member is provided with an inset cutter 20 embedded therein adjacent the anchor member 9, said cutter having an edge 21 below adjacent surfaces of the elongate base member 2 with a recess 22 permitting access to the cutting edge for cutting strands of dental floss. The arrangement of the cutter and recessed relation provides safety as it substantially prevents accidental contact of a person with the cutting edge 21.

The fingers or extenders 3 and 4 together with said one end portion 5 of the base member 2 form a head 23 adapted to be moved into the mouth of a user and positively positioned and moved permitting manipulation of the dental floss strand 8 yet the fingers or extenders are relatively thin and the one end portion of the base member is relatively small so as to permit viewing of the floss strand 8 as it is being used.

In using a dental floss applicator constructed as described, one end of a strand of dental floss is connected to the anchor member 9 and extended therefrom over one side portion 19 to a shoulder 18 on the other side and then down through the respective groove 17 and along the outer surface 15 of a finger 3 and then engaged with a floss receiving portion or slit 6 at the free end of said finger. The floss strand extends from said finger 3 to the receiving portion or slot 6 of the other finger 4 and is engaged therewith and then extended in engagement with the outer surface 15 of said other finger 4 through the respective groove 17 and engaged with a shoulder 18 thereof and then across the surface 13 to the other side to the cut-away 19 and to the anchor 9 and the other end of the strand is secured thereto. In applying the strand of dental floss and with the one end secured in engagement with the shoulders and slits or floss receiving portions 6, the strand may be tensioned as desired. The handle portion 11 is then grasped with one hand of the user and the applicator head 23 moved into the mouth and maneuvered to place the floss strand 8 between the teeth. The applicator head and the shape and size of the fingers or extenders permits the placing of strand 8 arranged between the finger ends 7 between the teeth with the fingers allowing the floss to roll over and along the sides of the gums and teeth to massage the gums and remove the solid food particles and such removal will aid in preventing plaque from forming on the teeth. The fingers 3 and 4 are shaped to fit over the teeth and are wide enough to slide at an angle sideways when placing floss between teeth that are very close together or when dental work has been performed and the space is very small. However, the applicator head is small enough to comfortably be placed over the back teeth of the person. The space between the strand 8 between the fingers and the base member 2 is greater than the height of any tooth so that the floss can be worked fully between the teeth. Fingers and base members at the head 23 form a U-shaped recess with diverging legs that facilitates the movement of the floss on the teeth. The back of the head is free of any protrusions and all of the structure that extends into the mouth has smooth surfaces on all sides. The anchor member 9 is spaced from the fingers 3 and 4 whereby it is outside of the area placed in the mouth, said anchor member being such as to hold the end of the floss strand from it. The fingers are rigid enough to hold the floss strand portion tight between the fingers, however, the fingers have some uni-directional flexibility to allow the floss portion between the fingers to shape to the contour of the gums and teeth while being used. Also the shape of the fingers is such that when placed fully over the teeth, the spacing prevents the floss from being pulled sideways between the teeth thereby eliminating the possible cutting of the gums. After use the dental floss is removed from the applicator and discarded then the entire structure may be washed or otherwise treated to maintain same clean and sanitary.

Figure 6:
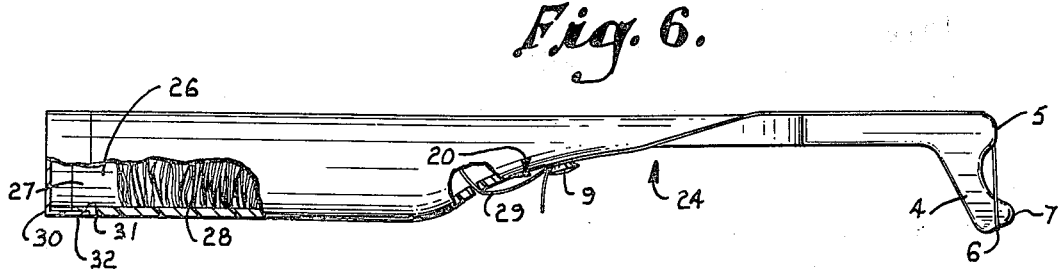
FIG. 6 is a side elevational view of a modified form of dental floss applicator with portions broken away to show the dental floss storage cavity therein.

In the form of the invention illustrated in FIG. 6 the structure of the applicator from the handle portion 24 to said one end 5 and including the fingers 3 and 4 and the guides and attachments of the dental floss strands are the same as illustrated and described relative to the structures shown in FIGS. 1 to 5 inclusive. The dental floss applicator 24 shown in FIG. 6 has a handle portion 25 enlarged with an elongate cavity 26 extending therein from an open end 27. The cavity is of a size to contain a spool 28 or other holder of a supply of dental floss 29. A cover 30 is removably mounted on the handle portion 25 to close said open end 27. In the structure illustrated, the handle adjacent the open end 27 has a reduced outer periphery as at 31 and the cover 30 has a flange 32 sleeved thereover and sealingly engaging same to provide a seal closure for the cavity 26. The use of the structure shown in FIG. 6 in the cleaning of teeth and gums is the same as that described relative to the structure shown in FIGS. 1 to 5 inclusive.

It is to be understood that while I have illustrated and described certain forms of my invention, it is not to be limited to the specific forms or arrangements of parts herein described and shown.

What I claim and desire to secure by Letters Patent is:

1. A dental floss applicator comprising:
   a. an elongate member having one end portion with a handle adjacent thereto and another end portion extending therefrom;
   b. a pair of laterally spaced apart fingers extending from said other end portion of said elongate member, said fingers and elongate member forming a U-shaped structure with said fingers diverging outwardly from said elongate member, said fingers enlarging in transverse thickness as they extend away from said elongate member forming a molar tooth shaped receiving cavity therebetween which is larger adjacent said elongate member than at a position spaced from said elongate member and permitting snug reception of a person's molar tooth therebetween;
   c. floss receiving transversely aligned recesses in free ends of said fingers;
   d. means at said other end portion of the elongate member forming shoulders facing away from the handle;
   e. anchor means on said elongate member spaced from said fingers for securing engagement with a strand of floss extending from said anchor means in engagement with a shoulder and then along a finger through a respective finger recess to the other finger recess then along the other finger to the shoulder and back to said anchor means.

* * * * *